United States Patent
Depenbusch

(10) Patent No.: US 10,898,374 B2
(45) Date of Patent: *Jan. 26, 2021

(54) CATARACT POSTERIOR/WEDGE CHOPPER

(71) Applicant: Michael Jerome Designs, LLC, Chandler, AZ (US)

(72) Inventor: Michael Jerome Depenbusch, Phoenix, AZ (US)

(73) Assignee: Michael Jerome Designs, LLC, Chandler, AZ (US)

( * ) Notice: Subject to any disclaimer, the term of this patent is extended or adjusted under 35 U.S.C. 154(b) by 176 days.

This patent is subject to a terminal disclaimer.

(21) Appl. No.: 16/195,690

(22) Filed: Nov. 19, 2018

(65) Prior Publication Data

US 2019/0083311 A1    Mar. 21, 2019

Related U.S. Application Data

(63) Continuation of application No. 14/983,518, filed on Dec. 29, 2015, now Pat. No. 10,166,144.
(Continued)

(51) Int. Cl.
*A61F 9/007* (2006.01)

(52) U.S. Cl.
CPC ...... *A61F 9/00763* (2013.01); *A61F 9/00745* (2013.01)

(58) Field of Classification Search
CPC .............. A61F 9/00736; A61F 9/00754; A61F 9/0133; A61F 9/00763; A61F 9/00745; A61B 17/32; A61B 17/3205; A61B 17/3209; A61B 17/320068; A61B 17/0069; A61B 17/0082; A61B 2017/320044;
(Continued)

(56) References Cited

U.S. PATENT DOCUMENTS

| 3,589,363 A | 6/1971 | Banko et al. |
| 4,623,327 A | 11/1986 | Mahurkar |

(Continued)

FOREIGN PATENT DOCUMENTS

WO    WO 2014/192584 A1    12/2014

OTHER PUBLICATIONS

PCT International Search Report and Written Opinion, PCT Application No. PCT/US16/40048, dated Oct. 31, 2016, 15 pages.
(Continued)

*Primary Examiner* — Melanie R Tyson
(74) *Attorney, Agent, or Firm* — Fenwick & West LLP

(57) ABSTRACT

Disclosed here is an apparatus and method for cataract surgery. The apparatus is an instrument referred to as a chopper that allows the reduction or elimination of ultrasound and/or laser energy introduced into the eye during cataract surgery. The chopper instrument is bent at an angle, such as an angle less than 110 degrees or less than 90 degrees, to provide a posterior (to anterior) chopping, and a wedge compression of the cataract. The bend in the chopper instrument, among other features, introduces refined vector forces that help in breaking/chopping the cataract with ease. The apparatus allows laser free/ultrasound free cataract extraction in dense cataracts. The chopper apparatus, a vacuum-tip and the proper vacuum settings, when used for performing a cataract surgery by a surgeon, allows the surgeon to break up the nucleus into small enough fragments that a true ultrasound-free/laser-free small incision cataract surgery can be accomplished with ease.

20 Claims, 8 Drawing Sheets

Related U.S. Application Data

(60) Provisional application No. 62/190,190, filed on Jul. 8, 2015.

(58) Field of Classification Search
CPC ....... A61B 2017/320056; A61B 2017/320072; A61B 2017/320073; A61B 2017/320069
See application file for complete search history.

(56) References Cited

U.S. PATENT DOCUMENTS

| | | | |
|---|---|---|---|
| 4,924,882 | A | 5/1990 | Donovan |
| 5,403,307 | A | 4/1995 | Zelman |
| 5,476,450 | A | 12/1995 | Ruggio |
| 5,718,676 | A | 2/1998 | Barrett |
| 5,725,495 | A | 3/1998 | Strukel et al. |
| 5,836,959 | A | 11/1998 | Seibel et al. |
| 6,280,423 | B1 | 8/2001 | Davey et al. |
| 9,492,634 | B2 | 11/2016 | Moehle et al. |
| 2004/0030303 | A1 | 2/2004 | Prais et al. |
| 2008/0058708 | A1 | 3/2008 | Akahoshi |
| 2009/0041924 | A1 | 2/2009 | Steube |
| 2011/0112466 | A1 | 5/2011 | Dimalanta |
| 2013/0023918 | A1 | 1/2013 | Mortlet |
| 2015/0201958 | A1 | 7/2015 | Krieger et al. |

OTHER PUBLICATIONS

PCT Invitation to Pay Additional Fees, PCT Application No. PCT/US16/40048, Sep. 1, 2016, 2 pages.

United States Office Action, U.S. Appl. No. 14/983,518, dated Jun. 11, 2018, 11 pages.

European Patent Office, Extended Search Report and Opinion, EP Patent Application No. 16821825.3, dated Feb. 18, 2019, seven pages.

US 10,898,374 B2

CATARACT POSTERIOR/WEDGE CHOPPER

CROSS REFERENCE TO RELATED APPLICATIONS

This application is a continuation of prior, co-pending U.S. patent application Ser. No. 14/983,518, filed on Dec. 29, 2015, which claims the benefit of U.S. Provisional Application No. 62/190,190 filed Jul. 8, 2015, which are each incorporated by reference in their entirety.

BACKGROUND

This invention relates generally to the field of cataract surgery, specifically to a chopper apparatus used in the cataract surgery.

In current modern day cataract surgery, a significant amount of energy is introduced into the eye to remove the cataract. This energy causes direct damage and collateral damage to the eye (killing the fragile non-reproducing endothelial cells of the cornea). The energy triggers an inflammatory response that is damaging to the fragile endothelial cells, causes pain, longer recovery time and cystoid macular edema (CME) (among other things). The main sources of energy entering the eye and causing damage during cataract surgery are from ultrasound and femtosecond laser used during the procedure to break apart or emulsify the cataract. An instrument referred to as a "chopper" is used in conjunction with ultrasound or laser energy. For example, a femtosecond laser can be used for phacofragmentation of the cataract and/or ultrasound can be applied with a phacoemulsification tip or probe (called a "phaco probe" or "phaco tip," or alternatively a "vacuum tip") that vibrates at ultrasonic frequency to emulsify the cataract while a pump aspirates particles of the cataract through the tip. The chopper is used with the laser or ultrasound energy to assist with chopping or breaking the cataract into fairly small pieces that can be extracted from the eye using the pump or vacuum of the phaco tip. However, since these procedures all require the use of laser or ultrasound, there is no way to avoid damage to the eye and the inflammatory response described above.

SUMMARY

Described here is an apparatus and method for cataract surgery. A chopper apparatus described here is an instrument used in performing the cataract surgery that allows the reduction of ultrasound and/or laser energy introduced into the eye to a low amount or completely eliminates use of ultrasound/laser during cataract surgery. The chopper apparatus includes a chopping member that an elongated member that is bent at an angle of 110 degrees or less, such as an angle of less than 90 degree (though it can be more than 110 degrees or much less than 90 degrees in some embodiments) to provide a posterior (to anterior) approach and a wedge compression of the cataract. The chopper member has a more substantial bend than prior chopper designs, and the bend (also referred to as a wedge or wedge portion) in the chopper member introduces refined vector forces that help in breaking/chopping the cataract with ease. In some embodiments, other features also contribute to the improved breaking of the cataract, including an increased length (relative to prior choppers) from the bend in the chopper member to the distal tip of the chopper member, sharp edges on one or both sides of the bend, among other improvements. In some embodiments, the chopper member includes or is attached to a handle that can be held by the user and used to manipulate the chopper apparatus to break the cataract. The chopper apparatus allows laser free/ultrasound free cataract extraction in dense cataracts. The chopper apparatus, a vacuum-tip and the proper vacuum settings, when used for performing a cataract surgery by a surgeon allow the surgeon to break up the nucleus of the cataract into small enough fragments that a true ultrasound-free/laser-free small incision cataract surgery can be accomplished with ease. Such a reduction or elimination of laser and ultrasound energy delivered to the eye during cataract surgery is the main variable to reduce direct damage, collateral damage and inflammation.

Eliminating the need for ultrasound and laser assistance in cataract surgery benefits the patient and also eliminates the need for large, heavy and expensive ultrasound or laser machines. In addition, the number of cataract surgeries that can be conducted in a given facility is not limited by the facility having only one or a few of these expensive machines for which each patient must wait to receive the surgery.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

General Cataract Surgery Summary

Figure 1:
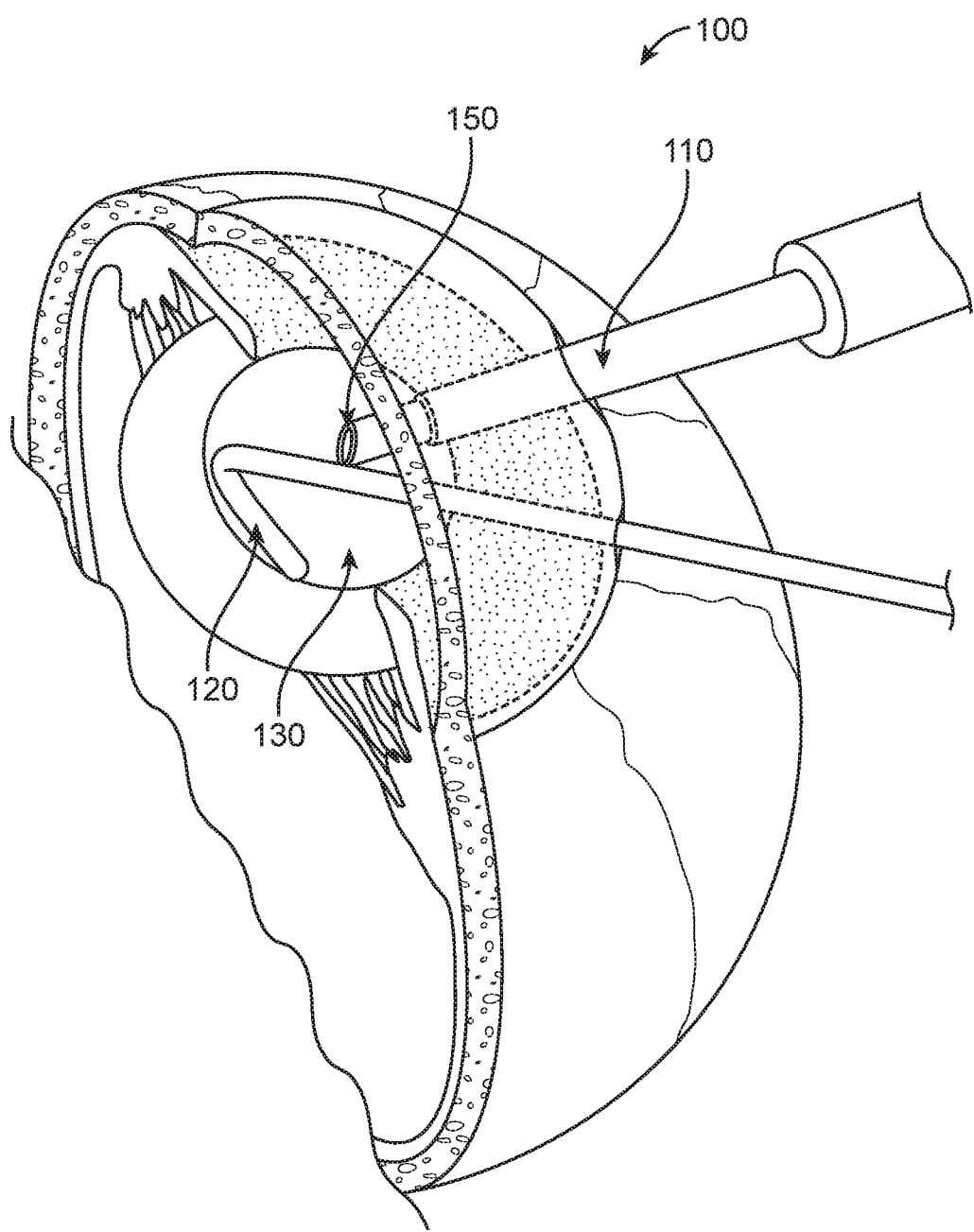
FIG. 1 illustrates a cross section view of a cataract surgery performed using the chopper and vacuum tip instruments, in accordance with an embodiment.

FIG. 1 illustrates a cross section view of a cataract surgery 100 performed using a chopper apparatus 120 and phacoemulsification probe 110 or vacuum tip instruments, in accordance with an embodiment. Cataract surgery is the removal of the natural lens of the eye that has developed an opacification (e.g. cloudiness), referred to as a cataract. During cataract surgery, a patient's cloudy natural lens is removed and replaced with a synthetic lens. To perform a cataract surgery, one or more small incisions are made at the corneal margin of the eye. Typically, a phacoemulsification probe 110 is inserted along with a chopper apparatus 120 to break and emulsify the cataract. The chopper apparatus 120 breaks the cataract into at least three to four fragments. The phacoemulsification probe 110 then emulsifies the cataract using ultrasound/laser energy and sucks up each fragment using a vacuum tip 150 for removal of the fragments from the eye. In some cases, a laser, such as a femtosecond laser, can be used during or at the beginning of the procedure to perform some fragmentation of the cataract. The laser may be used instead of or with the ultrasound to perform the micro-chopping or emulsification of the cataract.

Once the cataract is chopped, fragmented/emulsified and sucked into the vacuum tip, an artificial foldable lens is inserted, and once inside, the lens unfolds in place of the natural lens. The small incision heals naturally without the need for sutures.

Figure 2:
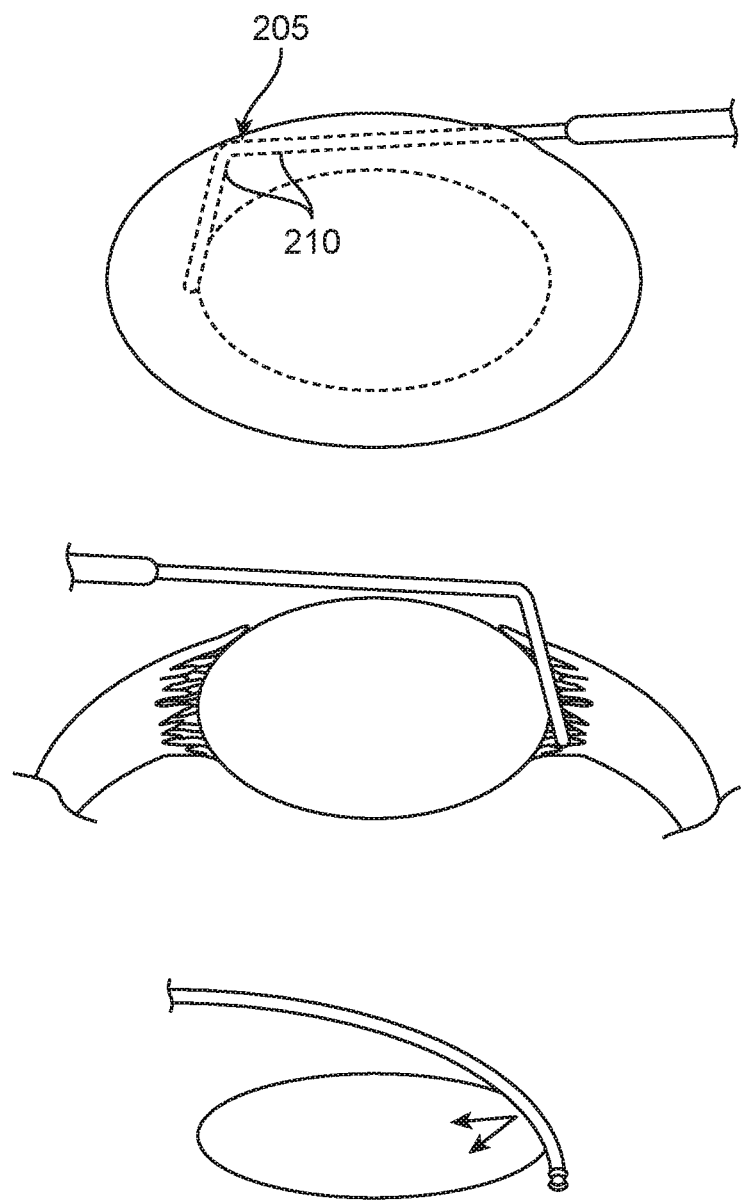
FIG. 2 illustrates a chopper instrument of the prior art.

FIG. 2 illustrates prior art chopper apparatus, in accordance with an embodiment. The prior art chopper apparatuses perform a horizontal chop that implements compressive force to break the cataract. The prior art choppers are bent at an angle 210 of greater than 110 degrees to create a bend 205 with an obtuse angle 210 that applies the compressive force. The prior art choppers do not completely wrap around the nucleus of the cataract leading to inefficient chopping technique.

Cataract Chopper Apparatus

Figure 3:
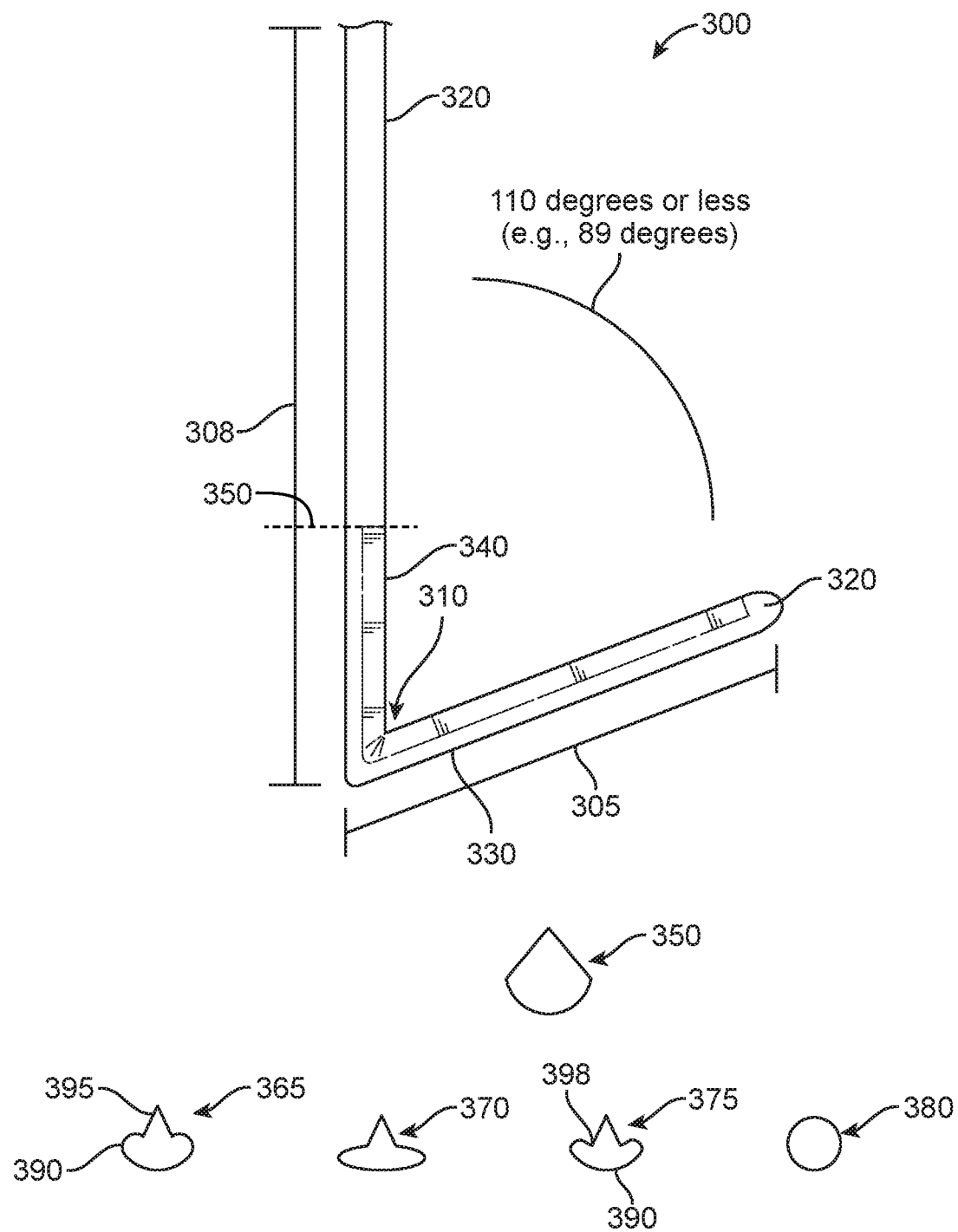
FIG. 3 illustrates a chopper instrument with refined vector forces to chop the cataract with ease, in accordance with an embodiment.

FIG. 3 illustrates a chopper apparatus 300 with refined vector forces to chop the cataract with ease, in accordance with an embodiment. The chopper apparatus 300 comprises a chopping member 302 that has a bend at the distal-most end to essentially form two portions on either side of the bend (e.g., a proximal portion closest to the handle of the instrument that is manipulated by the surgeon and a distal portion closest to the patient). The proximal portion is referred to here as an arm 308 and the distal portion is referred to as a forearm 305. The forearm 305 may be of size 1.0 mm or longer. In some embodiments, the forearm 305 is 1.0 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 3 mm, or longer (or any value or fractional value in between these numbers). The arm 308 and the forearm 305 create a wedge 310 or a bend that is at an angle 110 degrees or less. In some embodiments, the angle is 110 degrees, 109 degrees, 108 degrees, 105 degrees, 100 degrees, 95 degrees, 90 degrees, 89 degrees, 88 degrees, 87 degrees, 86, degrees, 85 degrees, 80 degrees, 75 degrees, 70 degrees, 65 degrees, 60 degrees, or less (or any value or fractional value in between these numbers). In one example of the chopper apparatus 300, the angle is less than 90 degrees to provide refined vector forces and a posterior approach for improved breaking of the cataract for removal.

The forearm 308 is shaped such that it can wrap around the nucleus tightly and with ease due to the 110 degree or less angular bend and the longer forearm. The equator of the nucleus is straddled in the wedge 310 between the forearm 305 of the chopper 300 and the arm 308 of the chopper, and so the wedge 310 can be positioned on the posterior of the nucleus to create mechanical vector forces that can easily break the cataract as the chopper apparatus is pulled across or through the cataract to chop the cataract (e.g., a posterior to anterior chopping action).

The forearm of the chopping member 302 ends with a tip 320 that is generally a blunt tip that can be rounded and can be smooth. The tip 320 is further used to propagate the breaks in the cataract fragments. An outside surface 330 of the chopping member 302 that faces outward from the bend of the chopping member 302 the extends along the arm portion 308, the forearm portion 305 or the wedge portion 310 is generally smooth and can be rounded (e.g., as shown in the cross sections 350, 365, 370, and 380), though it can have a flattened surface (e.g., as shown in the cross section 370). An inside edge 340 facing into the bend of the chopping member 302 can be smooth and rounded (e.g., as shown in cross section 380) or can be sharp (e.g., as shown in cross sections 350, 365, 370, and 375). The inside edge 340 can extend part of or the entire length of the forearm portion 305 to the blunt end or tip 320 of the forearm portion. Where the inside edge 340 is a sharp edge, the sharp edge can be used to help break or cut the tissue of the cataract into fragments.

FIG. 3 also illustrates various different cross sections of the chopper apparatus 300, according to different embodiments. The cross section 350 of the forearm shows a rounded outside surface 330 and a sharp inside edge 340 of the chopper apparatus 300. This is the cross section of the chopper apparatus 300 as illustrated by a dotted line showing the location in the apparatus from which the cross section is taken. The other cross sections 365, 370, 375, 380 are alternative embodiments showing different inside and outside edges that can be mixed and matched as desired. In the cross section 350, he sharp edge 340 extends from the rounded surface to form a continuous line as illustrated in FIG. 3. In the embodiments illustrated in the cross sections 365 and 375, the outside surface 330 is a rounded surface that has a lip 390 formed on either side of the sharp inside edge 340. In 365, the lip 390 extends somewhat toward the point of the sharp edge to form a bulbous lip that is continuous with the rounded surface of the outside edge. In 375, the sharp edge is recessed into the chopping member such and the lip 390 is narrower than the lip in 365, and the lip in 375 reaches toward a tip or point 395 of the sharp edge and a divet or cavity 398 is formed on either side of the sharp edge between the edge and the lip 390. In another embodiment show in cross section 370, the inside edge 340 is a sharp edge and the outside surface 330 is a flat surface extending laterally out from either side of the sharp edge 340. Cross section 380 illustrates the inside edge as a rounded surface that is continuous with the outside edge to form a round design. It can also take on other shapes, such as oval or irregular shapes designed to break the cataract. Alternate embodiments of the chopper 300 can have different cross sections or different combinations of the components shown in the cross sections illustrated in FIG. 3 (such as a rounded inside edge with a flattened outside edge).

Figure 4A:
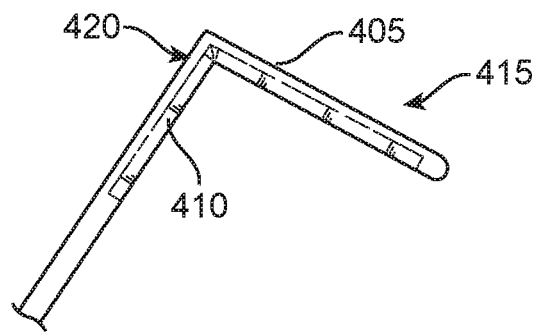
FIG. 4A illustrates a sharpened inside edge and outside edge of the chopper instrument, in accordance with an embodiment.

FIG. 4A illustrates a sharpened inside edge and a rounded outside edge of the chopper apparatus, in accordance with an embodiment. The chopper apparatus includes a chopping member that has two inside edges, one for the forearm 405 and one for the arm 410. Similarly there are two outside surfaces, one for the forearm 415 and one for the arm 420. The figure shows sharpened inside edges 405 and 410 and rounded outside edges for the forearm 415 and the arm 420. Alternatively, one of the inside edges may be sharp and the other may be blunt. For example, the inside edge of the forearm 405 may be sharp and the inside edge of the arm 410 may be blunt. Similarly, any of the edges shown at the bottom of FIG. 3 can be used, and the arm 410 and forearm 405 can have different edges, or the edges may vary in type along the length. The outside edges are generally smooth. They may be rounded or flat or curved. Similar to the inside edges, one of the outside edges may be different from the other, for example, the outside edge of the arm 420 may be rounded and smooth and the outside edge of the forearm 415 may be rounded and flat.

The length of the inside edge, or in some cases the sharp portion, can also vary. In the embodiment shown in FIG. 3, the sharp portion of the forearm 330 extends from the wedge 310 to the tip 320. However, the sharp portion can start at the wedge and end anywhere along the length of the forearm 305 (such as halfway up the forearm 305). The sharp portion can also start at the tip 320 and may not extend all the way to the wedge 310 but can end anywhere along the length of the forearm 305. The same is true for the sharp portion of the arm 308 that can start at the wedge or not, and can end anywhere along the length of the arm 308. For example, it might extend the same distance up the arm portion as it extends up the forearm portion such that the sharp portion is an equal distance from the bend on either side. In one embodiment, the sharp portion of either the forearm 305 or the arm 308 is 5 mm, 4 mm, 3 mm, 2.5 mm, 2 mm, 1.5 mm, 1.0 mm, 0.5 mm or less, or any value or fractional value in between). In some embodiments, the inside edge 340 is present only on one of the forearm and arm portions.

Figure 4B:
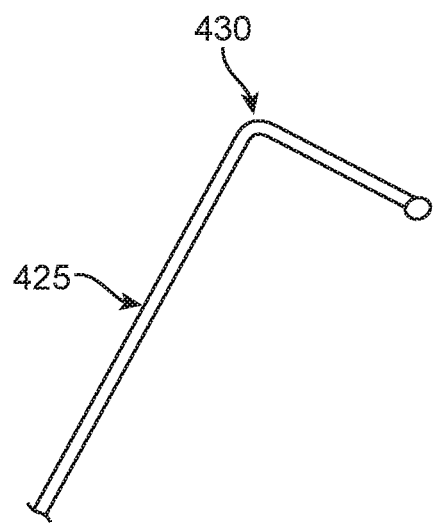
FIG. 4B illustrates a straight handle of the chopper instrument, in accordance with an embodiment.

FIG. 4B illustrates a straight handle 425 of the chopper instrument, in accordance with an embodiment. In alternate embodiments, the handle 425 may be bent at an angle. The elbow 430 to tip length is generally 1.0 mm to 2.0 mm, though it can be longer as described above. The longer length allows the nucleus to be straddled easily and creates mechanical forces that can easily break the cataract.

Figure 5A:
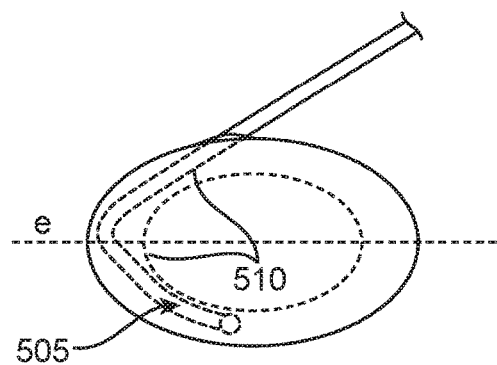
FIGS. 5A-5C illustrate a chopper instrument wrapped around a nucleus of a cataract to chop/break the cataract, in accordance with an embodiment.
Figure 5B:
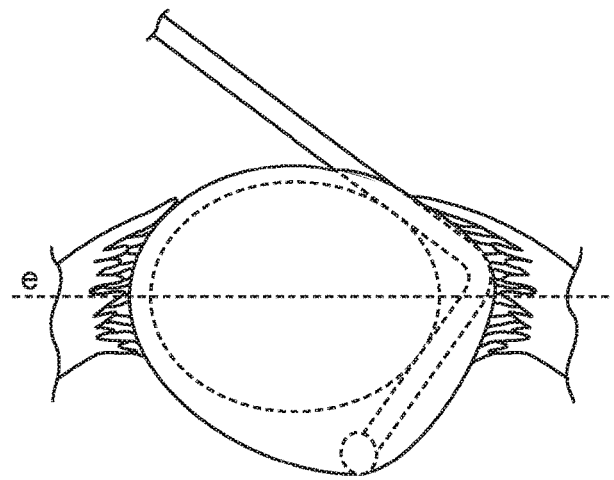
Figure 5C:
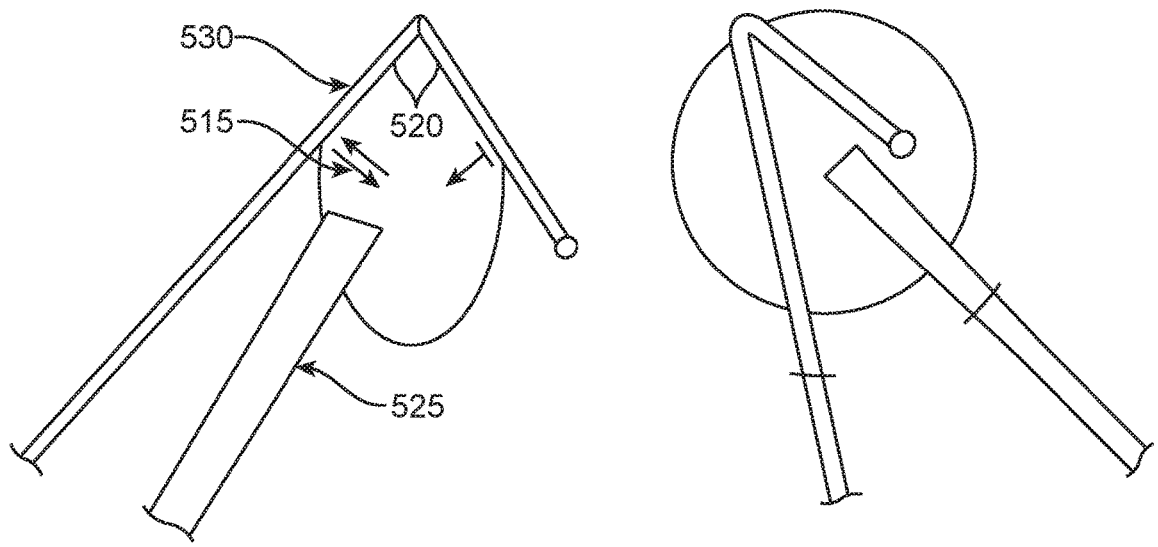

FIG. 5A-5C illustrate a chopper instrument wrapped around a nucleus to chop/break the cataract, in accordance with an embodiment. FIG. 5A shows the equator e of the nucleus straddled in the forearm 505 of the chopper instrument. This is an anterior view of the cataract, and a posterior view might be illustrated similarly. The position of the chopper apparatus, however, may be such that the arm or forearm is positioned somewhat on the posterior side of the nucleus, and the other part of the chopper may be more on the anterior side of the nucleus. Due the angular bend 510 of 110 degrees or less and the longer forearm, the nucleus can be easily straddled in the forearm 505 of the chopper instrument. Similarly FIG. 5B shows the reach of the forearm from a different side. FIG. 5C illustrates the reach of the forearm of the chopper along with the mechanical vector forces 515 created due to the angular bend 520 of 110 degrees or less. The figure illustrates the vacuum tip 525 that is used along with the chopper instrument to perform the cataract surgery. The chopper 530 performs a horizontal chop on the cataract from a posterior of the nucleus to the anterior. The mechanical vector forces 520 easily chop the nucleus as opposed to outgoing forces that occur when the angle is greater, such as greater than 90 degrees or greater than approximately 110 degrees. The vacuum tip 525 easily sucks the broken fragments into the tube since the chopper keeps the fragments straddled in the forearm of the chopper 530.

Various different types of vacuum or phaco tips can be used with the chopper instrument 120. In one embodiment, the chopper instrument 120 is used with a vacuum tip that is designed for efficient vacuum removal by including a lumen that has a diameter larger than the tip opening or that increases in diameter past the opening, as is described in U.S. Provisional Application No. 62/190,224, filed on Jul. 8, 2015, which is hereby incorporated by reference herein in its entirety. This vacuum tip can be one that does not apply any energy to the eye but simply applies vacuum for removal of the cataract tissue fragments.

Figure 6A:
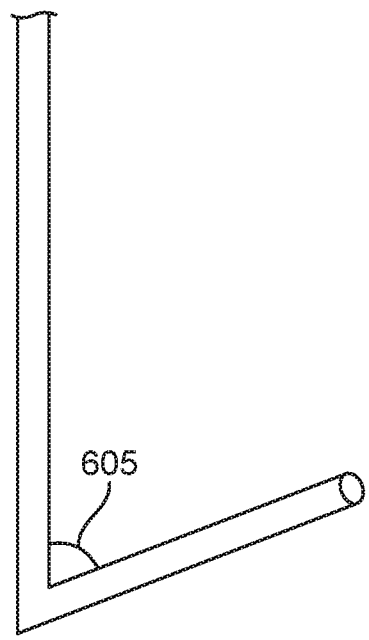
FIG. 6A illustrates a chopper with a paddle wedge, in accordance with an embodiment.

FIG. 6A illustrates a chopper with a paddle wedge extending out from the bend of the chopper, in accordance with an embodiment. In this embodiment, the surface area along the wedge may be wider laterally than the area along the rest of the forearm or the arm of the chopper instrument to form a paddle shape at the wedge. This is referred to here as a wedge paddle 605 or paddle. The wedge paddle helps maneuver soft cataracts that may be easier to scoop out rather than breaking/chopping. In one embodiment, the wedge paddle 605 extends laterally on either side of the chopping member to form a scoop design for scooping the soft cataracts. The wedge paddle 605 design thereby increases the width or surface area of the chopper apparatus such that it is more of a paddle or scoop shape that is moved from the posterior to anterior through the cataract rather than the thinner rod-like design of the chopper apparatus without the wedge paddle 605. In a further embodiment, the paddle can extend out from the wedge, arm, or forearm into the bend of the chopper apparatus to increase the height of the chopper apparatus.

Figure 6B:
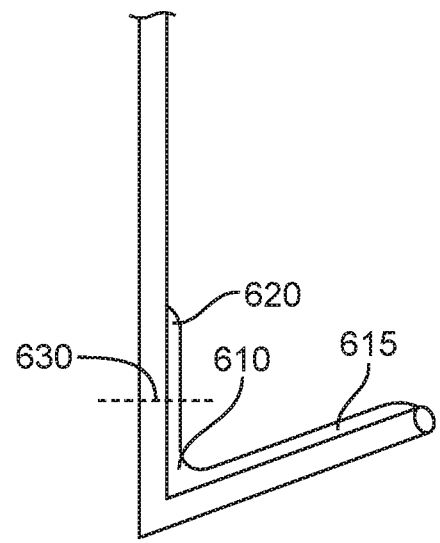
FIG. 6B illustrates a chopper with a paddle wedge along the length of the handle and forearm and a cross section view of the same, in accordance with an embodiment.
Figure 6B:
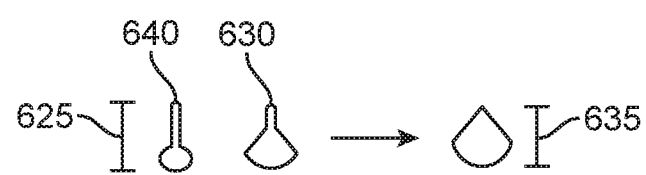

FIG. 6B illustrates a chopper with a paddle wedge along the length of the arm and forearm a certain distance, and a cross sectional view of the same, in accordance with an embodiment. In this embodiment, the surface area along part of or the entire length of the arm 620, forearm 615, and wedge 610 is increased to help with maneuvering soft cataracts. As shown in the cross section view 630 of the paddled forearm and wedge, the height of the wedge paddle 625 (also shown at 635) and also the width may be around 0.5 to 3.0 mm (e.g., 0.6 mm, 0.7 mm, 0.8 mm, 0.9 mm, 1.0 mm, 1.5 mm, 2 mm, and so forth, including any value or fractional value in between) and the inside edge of the forearm 635 may be around 0.3 to 0.5 mm (including any value or fractional value in between). For example, the width at the widest portion of the paddle might be 3.0 mm and the width at the narrowest portion or inside edge might be 0.3 mm. The width of the paddle can also be larger at some locations on the chopper apparatus (e.g., up to 5 or 10 mm or more.). In other embodiments, the paddle portion is present only at the arm 620 or only at the forearm 615. The paddle portion can extend various lengths along the arm 620 or the forearm including the same distances that were described above for the lengths that the sharp edge extends along the arm 620 or forearm 615. The paddle can vary in shape and size along the length and can be different for the forearm 615 versus the arm 620. For example, the paddle can be widest at the wedge or elbow of the chopper apparatus, and can decrease in width as it moves farther from the wedge along the arm or forearm. In some embodiments, the paddle extends laterally from one or more of the wedge portion, the arm, and the forearm, though the paddle could also extend laterally from the inside edge on top of the wedge, arm, or forearm, and thus could rest on top of the wedge, arm, or forearm facing into the bend of the chopping member.

At the bottom of FIG. 3 is shown cross section 630, and a dotted line through the chopper apparatus illustrates from where this cross section is taken in the device. Alternate embodiments of the paddle portion are shown in the cross sectional views 640 and 635. Cross section 640, for example, has a longer inside edge at the top and a smaller, more rounded arm of the chopper apparatus than is shown in cross section 630. Cross section 635 shows the inside edge as generally continuous with the arm of the chopper apparatus. It appears similar to the cross section 350 of FIG. 3, but it can be substantially wider at the base to form more of a paddle or scoop shape.

Cataract Surgical Procedure

Figure 7:
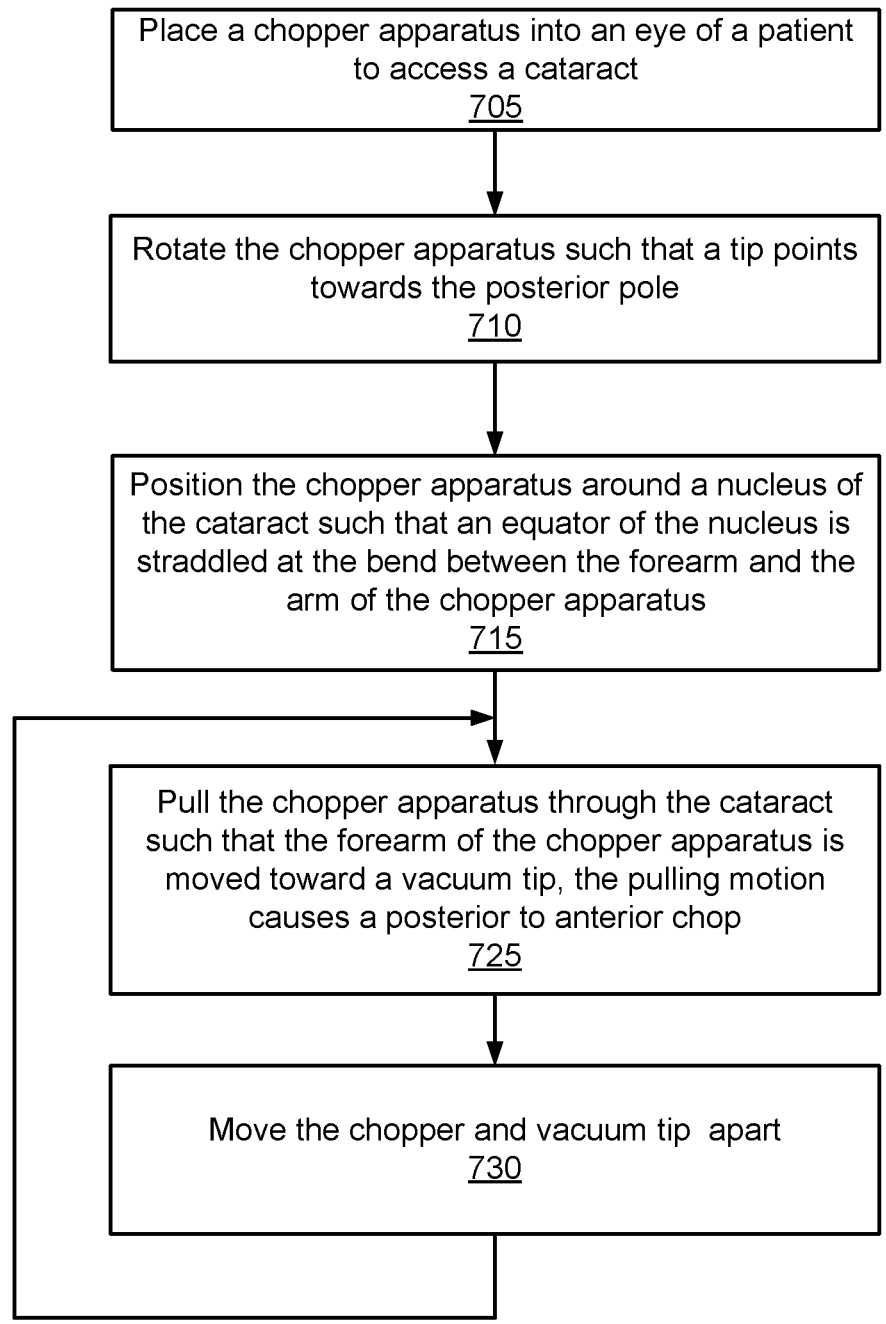
FIG. 7 illustrates a flowchart of a method for performing ultrasound free cataract surgery using the chopper instrument, in accordance with an embodiment.
Figure 8A:
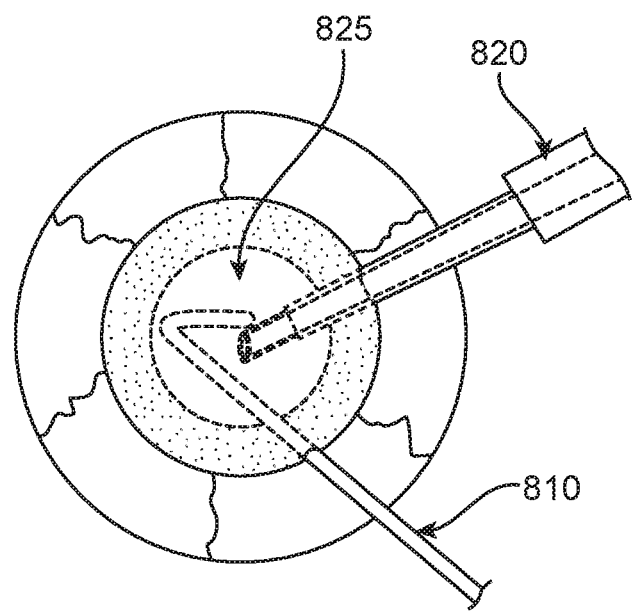
FIGS. 8A-8B illustrate a chopper instrument and a vacuum tip used to perform an ultrasound free/laser free cataract surgery, in accordance with an embodiment.
Figure 8B:
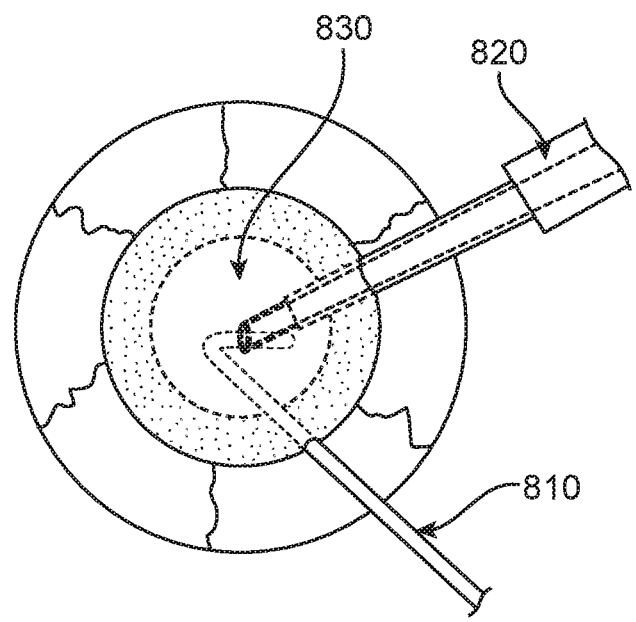

FIG. 7 illustrates a flowchart of a method for performing ultrasound and laser free (or limited ultrasound/laser) cataract surgery using the chopper instrument, in accordance with an embodiment. FIG. 8A-8B illustrate a chopper instrument and a vacuum tip used to perform an ultrasound free/laser free cataract surgery, in accordance with an embodiment. A chopper apparatus is placed 705 into an eye of a patient to access a cataract. Specifically, two incisions are made in the cornea, one larger incision (sometimes called the "cataract incision") for insertion of the larger vacuum tip instrument for removal of the cataract fragments once the chopping procedure has been performed, and one smaller incision for insertion of the chopper apparatus (see, e.g., FIG. 1 illustrating the incisions). In addition, a capsulorrhexis or capsulotomy is used to create an opening in the lens capsule to access the lens within the capsule, and a hydrodissection is performed to free the cataract from the lens capsule. The hydrodissection allows rotation of the nucleus of the cataract within the lens capsule. The chopper apparatus 810 is then placed through a sideport and under the capsulorrhexis horizontally.

As the chopper apparatus 810 approaches the equator of the nucleus (approximately 180 degrees away from the corneal incision and usually under the iris), the chopper apparatus 810 is rotated 710 such that the tip of the chopper apparatus at the distal end points towards the posterior pole of the eye. The chopper apparatus 810 is positioned 715 around the nucleus 825 of the cataract such that the equator of the nucleus 825 is straddled at the bend between the forearm of the chopper and the arm of the chopper apparatus 810 with the forearm positioned at a posterior of (e.g., behind) the nucleus 825 and the arm positioned anteriorly on (e.g., in front of) the nucleus 825. The tip is tilted anteriorly from a posterior position of the cataract such that the tip points toward the corneal incision (e.g., pointing generally toward the larger of the two corneal incisions, the incision for the vacuum tip), as shown in FIG. 8A. This position allows for the forearm of the chopper apparatus to be posterior to the nucleus and the most horizontal portion of the nucleus (e.g., farthest from the larger of the two corneal incisions, the incision for the vacuum tip) is positioned within the elbow or bend of the chopper apparatus.

With the vacuum tip 820 placed proximal to the center of the anterior surface of the nucleus 825, the forearm of the chopper apparatus 810 positioned posteriorly on the nucleus 925 is then pulled 725 horizontally and anteriorly simultaneously through the cataract toward the center of the phaco or vacuum tip 820 until the chopper apparatus 810 and the vacuum tip 820 are nearly touching. For example, the forearm of the chopper positioned at the posterior or back of the nucleus can be moved toward the anterior or front of the nucleus while also being moved horizontally (e.g., from a location on the cataract farthest from the larger of the two corneal incisions to a generally central location in the cataract near the vacuum tip, or generally to the other side of the cataract closest to the larger incision). The position of the forearm allows a posterior to anterior vector force that provides a better leverage to the physician to slice through or fragment the cataract tissue. The design of the chopper apparatus 810 allows the vector forces created by the chopper on the nucleus 825 to point anteriorly against the vacuum tip 820, causing a posterior to anterior chop 830 of the nucleus 825 as shown in FIG. 8B. No vacuum is needed to keep the nucleus in place as the chopper continues to approach the vacuum tip. The chopper apparatus 810 and vacuum tip 820 are moved 730 apart in a horizontal direction, i.e., the chopper in a horizontal and anterior direction, to fragment the nucleus. A complete fragment from equator to equator is desired but not necessary. The nucleus can now be rotated and the pulling and moving apart of the chopper apparatus 810 is repeated to cause more fragments in the nucleus.

Typically the nucleus is broken into 5 to 8 fragments with this method of FIG. 7. The fragments are then fixated and freed from other fragments with the vacuum tip. The vacuum tip simultaneously performs micro-chopping and feeding of the pieces directly into the vacuum tip, but the micro chopping can be performed without laser or ultrasound. Examples of vacuum pumps that can be used with the vacuum tip include a venturi pump and a peristaltic pump.

Additional Configuration Considerations

Throughout this specification, plural instances may implement components, operations, or structures described as a single instance. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the patent rights be limited not by this detailed description, but rather by any claims that issue on an application based hereon.

Upon reading this disclosure, those of skill in the art will appreciate the apparatus and method for performing a cataract surgery through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for performing an ultrasound and laser free cataract surgery using a chopper apparatus including a bend near a distal end, the method comprising:
   placing the chopper apparatus into an eye of a patient to access a cataract;
   rotating the chopper apparatus such that a tip of the chopper apparatus at the distal end points toward a posterior pole of the cataract;
   positioning the chopper apparatus around a nucleus of the cataract such that an equator of the nucleus is straddled at the bend; and
   fragmenting the nucleus into a plurality of fragments.

2. The method of claim 1, further comprising:
   removing the plurality of fragments from the eye using a vacuum tip.

3. The method of claim 2, further comprising:
   freeing the plurality of fragments from one another; and
   simultaneously fragmenting the nucleus and feeding at least one of the plurality of fragments into the vacuum tip for removal from the eye.

4. The method of claim 2, further comprising:
   cutting a first incision in a cornea of the eye for insertion of the chopper apparatus; and
   cutting a second incision in the cornea of the eye for insertion of the vacuum tip, the second incision larger than the first incision.

5. The method of claim 1, further comprising:
   performing hydrodissection by rotating the nucleus to free the cataract from a lens capsule of the eye.

6. The method of claim 1, wherein fragmenting the nucleus into the plurality of fragments comprises repeatedly chopping the nucleus by the chopper apparatus in a posterior-to-anterior motion.

7. The method of claim 1, wherein the bend is at an angle less than 110 degrees and greater than or equal to 90 degrees.

8. The method of claim 1, wherein the bend is at an angle less than 90 degrees.

9. The method of claim 1, wherein the plurality of fragments includes five to eight fragments.

10. The method of claim 1, wherein the chopper apparatus includes a wedge paddle formed at the bend, the wedge paddle extending laterally on either side of the chopping apparatus to form a scoop design, the method further comprising:
    maneuvering the cataract using the wedge paddle.

11. The method of claim 10, wherein the wedge paddle increases a surface area of at least a portion of the chopper apparatus.

12. The method of claim 10, wherein the wedge paddle includes at least a sharp edge and a smooth edge.

13. A method for performing cataract surgery using a chopping apparatus, the method comprising:
    placing the chopper apparatus into an eye to access a cataract, the chopping apparatus including a bend near a distal end of the chopping apparatus;
    rotating the chopper apparatus such that a tip of the chopper apparatus at the distal end points toward a posterior pole of the cataract;
    positioning the chopper apparatus around a nucleus of the cataract such that an equator of the nucleus is straddled at the bend between a forearm and an arm of the chopper apparatus with the forearm positioned at a posterior of the nucleus; and
    fragmenting the nucleus into a plurality of fragments for removal from the eye with a vacuum tip positioned near a center of an anterior surface of the nucleus, the fragmentation performed by repeatedly:
    pulling the chopper apparatus through the cataract such that the forearm of the chopper apparatus is moved anteriorly and horizontally toward a vacuum tip, the pulling motion causing a posterior to anterior chopping of the nucleus.

14. The method of claim 13, further comprising:
    removing the plurality of fragments from the eye using the vacuum tip with a venturi pump or a peristaltic pump.

15. The method of claim 13, further comprising:
    freeing the plurality of fragments from one another; and
    simultaneously fragmenting the nucleus and feeding at least one of the plurality of fragments into the vacuum tip for removal from the eye.

16. The method of claim 13, further comprising:
    cutting a first incision in a cornea of the eye for insertion of the chopper apparatus; and
    cutting a second incision in the cornea of the eye for insertion of the vacuum tip, the second incision larger than the first incision.

17. The method of claim 13, further comprising:
    performing hydrodissection by rotating the nucleus to free the cataract from a lens capsule of the eye.

18. The method of claim 13, wherein the chopper apparatus includes a wedge paddle formed at the bend, the wedge paddle extending laterally on either side of the chopping apparatus to form a scoop design, the method further comprising:
    maneuvering the cataract using the wedge paddle.

19. The method of claim 18, wherein the wedge paddle increases a surface area of at least a portion of the chopper apparatus.

20. The method of claim 18, wherein the wedge paddle includes at least a sharp edge and a smooth edge.

* * * * *